United States Patent [19]

Izumi

[11] Patent Number: 4,622,077
[45] Date of Patent: Nov. 11, 1986

[54] METHOD OF CLEANING THE INSIDE OF A ROOM

[76] Inventor: Masahiko Izumi, 13-14, 2-chome, Nishimagome, Oota-ku, Tokyo, Japan

[21] Appl. No.: 753,583

[22] Filed: Jul. 3, 1985

Related U.S. Application Data

[63] Continuation-in-part of Ser. No. 591,792, Mar. 21, 1984, abandoned.

[51] Int. Cl.$^4$ .............................................. B08B 3/00
[52] U.S. Cl. .................... 134/36; 134/22.11; 239/338
[58] Field of Search ........... 134/34, 36, 22.11; 239/338, 427.3, 429, 430, 431, 432, 433, 434; 261/118; 55/84

[56] References Cited

U.S. PATENT DOCUMENTS 3,266,934  8/1966  Alexander .......................... 134/36
4,251,033  2/1981  Rich et al. ......................... 239/338
4,301,970  11/1981  Craighero ......................... 239/338

Primary Examiner—George Yeung
Attorney, Agent, or Firm—Browdy and Neimark

[57] ABSTRACT

An air, containing 2,000,000 or more mist particles per cubic foot with particle sizes of essentially not more than 0.5 microns, cleans the inside of a room. The air is sent to the room and then removed therefrom, thereby the mist particles carry dust, microorganism and the like therein out of the room.

The mist-containing air is created as follows: Water is injected at a pressure of 0.3 to 5.5 kg/cm$^2$ from a plurality of nozzles in order to cause the water to strike against the side wall of the water injection apparatus, the side wall being 10 to 150 cm away from the nozzles, and thereby form a large number of mist particles, and then circulating air therethrough to create said mist-containing air.

3 Claims, 6 Drawing Figures

METHOD OF CLEANING THE INSIDE OF A ROOM

This application is a continuation-in-part application of application Ser. No. 591,792 filed Mar. 21, 1984, now abandoned.

BACKGROUND OF THE INVENTION

The present invention relates to a method of cleaning factories manufacturing LSIs or VLSIs, factories manufacturing biopharmaceuticals, surgical operating rooms, precision machinery-washing factories and factories manufacturing sterile food, or objects placed in these factories and rooms, as well as the operatives, patients and the like therein wearing clothes.

More particularly, the invention pertains to a method wherein air, containing 2,000,000 mist particles or more of essentially not more than 0.5 micron per cubic feet, is sent to VLSI-manufacturing factories, sterile food-manufacturing factories, air-shower rooms in these factories into which operatives go before the commencement of work, or the sickrooms of seriously ill patients, to clean objects.

In general, hospitals, pharmaceutical-manufacturing factories, laboratories and so forth require a clean atmosphere containing no dust or microbes. Therefore, a means is employed such that air is cleaned by the use of an air filter or an air curtain is installed at the entrances and exists thereof. However, these means cannot provide a sufficiently cleaned gas, and the employment of an air-shower room still cannot attain the purpose of providing such a clean gas.

The present inventor has found, as one result of a zealous study into the cleaning of objects, that the smaller a waterdrop, the lower its surface tension and that when a waterdrop becomes a mist particle of 0.5 micron or less, it adheres strongly to microscopic objects, and, moreover, if a gas containing 2,000,000 or more such mist particles per cubic feet is applied to an object, the gas adheres not only to microscopic dust, but also to viruses as well as bacteria, mold fungi, and spores present therein and carries them away, thereby allowing the object to be cleaned. Moreover, it has been found that a gaseous atmosphere in which such microscopic waterdrops are suspended can clean the atmosphere as well as offer such the unexpected advantageous effect that although there are waterdrops present, the object will never be wetted even if the number of mist particles is larte, provided that each of the mist particles is essentially not more than 0.5 micron. It has also been found, as the result of further examinations, that when an ordinary gas is passed through a gaseous atmosphere in which are suspended microscopic water drops, the ordinary gas is highly cleaned so that it is ultraclean, and such a highly cleaned gas can be directly applied to various rooms, sections and other related places. The present invention has been completed on the basis of this new knowledge, and as the result of the repetition of various experiments and researches concerning, in particular, an industrially effective method of producing a gas in which are suspended microscopic waterdrops.

SUMMARY OF THE INVENTION

Accordingly, it is a primary object of the invention to provide a method of cleaning the inside of a room wherein inside thereof is treated with a gas in which are suspended a large number of mist particles of essentially not more than 0.5 micron.

The air within which a large number of mist particles of essentially not more than 0.5 micron are suspended, employed in the present invention, can be produced by means of an apparatus such as that described hereinafter. It is a matter of course that when an inert gas is required, it is only necessary to employ nitrogen gas instead of air.

DESCRIPTION OF THE PREFERRED EMBODIMENTS

The present invention relates to a method of cleaning the inside of a room, comprising:

injecting water at a pressure of 0.3 to 5.5 kg/cm$^2$ (gage pressure), more preferably 0.5 to 2.5 kg/cm$^2$, from a plurality of nozzles of an injection pipe located at the center of a water injection apparatus, the injection opening of the nozzles being in the range of 0.2 to 8 mm in diameter, more preferably 0.5 to 3 mm, in order to cause the water to strike against the side wall of the water injection apparatus, the side wall being 10 to 150 cm away from the nozzles, and thereby form a large number of mist particles;

circulating air through said formed mist particles to create a suspension of 2,000,000 or more mist particles, more preferably 5,000,000 or more, most preferably 10,000,000 or more, per cubic foot of air with particle sizes of essentially not more than 0.5 microns, while simultaneously separating from said suspension particles of said formed mist of larger size than 0.5 microns by centrifugal effect due to the circulation of air; and circulating the resulting gas-water suspension created in the water injection apparatus through the room.

Figure 1:
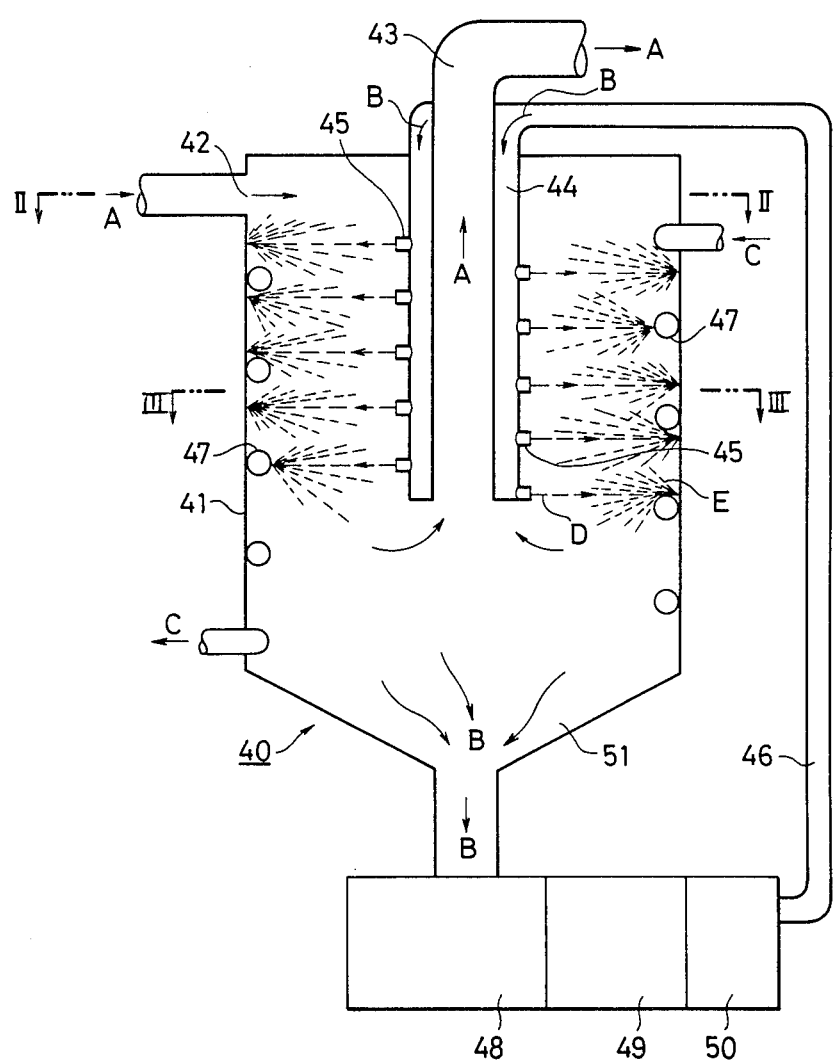
FIG. 1 shows an apparatus producing a mist-containing gas.
Figure 2:
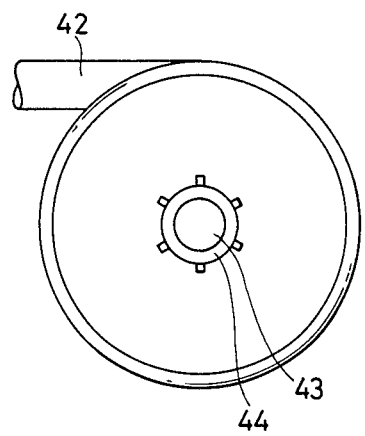
FIG. 2 is a section through the upper part of the apparatus of FIG. 1.
Figure 3:
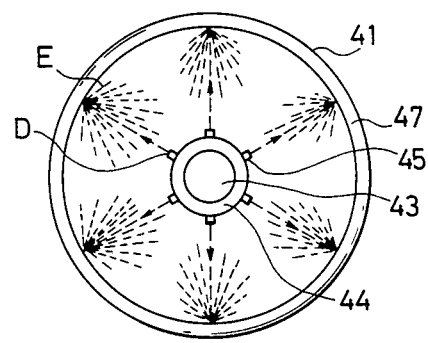
FIG. 3 is a section through the apparatus of FIG. 1, taken along the central part thereof.

FIGS. 1, 2 and 3 in combination show an efficient apparatus for producing a gas in which a mist is suspended, with which the temperature is controlled.

As an example, the production of a cooled mist-containing air will be described hereinunder. It is to be noted that a heated mist-containing air can be easily produced by replacing the following cooling system with a heating system.

A water injection apparatus 40 has an air inlet 42 tangentially provided in an upper part of a cylindrical portion 41 thereof. The center of the cylindrical portion 41 is provided with an outlet pipe 43 which extends downward. The outlet pipe 43 is provided with a water injection pipe 44 surrounding the outlet pipe 43, coaxially therewith. The injection pipe 44 is provided with a plurality of nozzles 45. An evaporation pipe 47 of a refrigerator is arranged within the cylindrical portion 41 of the cyclone 40. The evaporation pipe 47 and the nozzles 45 can be arranged so that the positions thereof are either completely or slightly offset from each other, and they are positioned so that the water from the nozzles 45 is injected perpendicularly onto the corresponding portions of the evaporation pipe 47 in the form of sprays or jets. The side wall is 10 to 150 cm away from the nozzles. A filter 48, a water tank 49 and a pump 50 are provided in that order in the lower end of a conical portion 51 of the water injection apparatus 40. Accordingly the cold water is recirculated in the direction of the arrows B, that is, through the sequence of the pump 50, a recirculation pipe 46, the injection pipe 44, the cylindrical portion 41 of the water injection apparatus, the conical portion 51 thereof, the filter 48, the water tank 49, and the pump 50. A refrigerant, in particular, a high-temperature refrigerant ($1°$ C. to $-5°$ C.), circulates through the evaporation pipe 47 in the direction of the arrows C. An air is sent into the water injection apparatus 40 through the inlet 42 in the direction of the arrow A, and it picks up microscopic waterdrops as is also cooled in the water injection apparatus 40 to become the required air which is then passed through the outlet pipe 43 for use. When the water injected, at D, from the nozzles 45 provided in the injection pipe 44, at a pressure of 0.3 to 5.5 kg/cm$^2$ (gauge pressure), more preferably 0.5 to 2.5 kg/cm$^2$, strikes the evaporation pipe 47 of the refrigerator and/or the side surfaces of the cylindrical portion 41, as at E (the side surfaces being 10 to 150 cm away from the nozzles), mist particles are produced (simultaneously therewith, the water stream striking the evaporation pipe 47 exchanges heat with the refrigerant flowing through the pipe 47 and is thus cooled), and the waterdrops are cooled. As the air passes through such an atmosphere, as shown by the arrows A, it picks up microscopic waterdrops as also exchanges heat with the cooled waterdrops so that it is cooled to create the air containing 2,000,000 or more mist particles, more preferably 5,000,000 or more, most preferably 10,000,000 or more, per cubic foot of air with particle sizes of essentially not more than 0.5 microns. The mist particles of larger size than 0.5 microns have been already separated by centrifugal effect due to the circulation of air.

Figure 4:
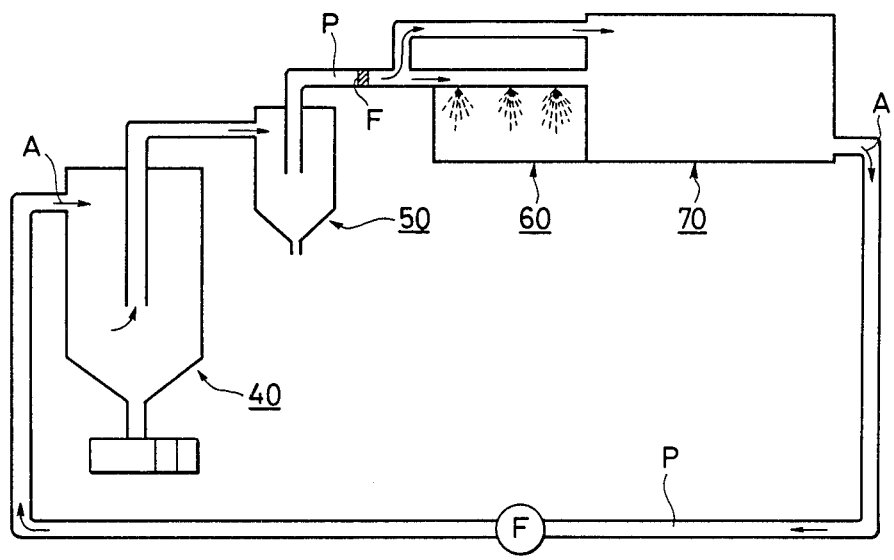
FIG. 4 is a schematic illustration of a complete system in which the present invention is applied to an actual semiconductor-manufacturing factory.

FIG. 4 is a schematic illustration of a complete system in which the method of the invention is applied in practice to a factory mass-producing 64-kilobit RAMs. The mist-containing air produced in the cyclone 40 by the operation described above is sent into a waterdrop-removing cyclone 50, as shown by the arrows A. More specifically, the air discharged from the cyclone 40 enters the water-drop-removing cyclone 50 through an inlet which is provided tangentially in a side wall of the cyclone 50. While the air is circulating in the water-drop-removing cyclone 50, excess waterdrops and large waterdrops are removed to provide air in which is suspended at least 90% mist particles of not more than $0.5\mu$, and the air is removed from an outlet pipe provided in the central part of the cyclone 50.

The mist-containing air thus removed is sent to an air-shower room 60 through a pipe P provided with a filter F (for removing off the mist particles of essentially more than 0.5 microns) to clean people who will work in an ultraclean room 70 adjacent to the air-shower room 60. Simultaneously, part of the mist-containing air is sent directly to the ultraclean room 70. Thus cleaned air which contains no dust is sent into the room and is also used to wash the silicon substrates employed in the manufacture of LSIs. The air which has been used in the ultraclean room 70 is removed therefrom and is returned to the cyclone 40 through a pipe P and a fan F, and the cycle is repeated. It has been confirmed that this method makes it possible to maintain an ultraclean room in such an extremely clean state that a space of 1 feet$^3$ contains less than one particle of dust bigger than $0.5\mu$. On the other hand, several tens of thousands of dust particles are suspended in a cubic foot of air in an ordinary factory. From this point of view, it will be understood that the method of the present invention is extraordinarily good.

Figure 5:
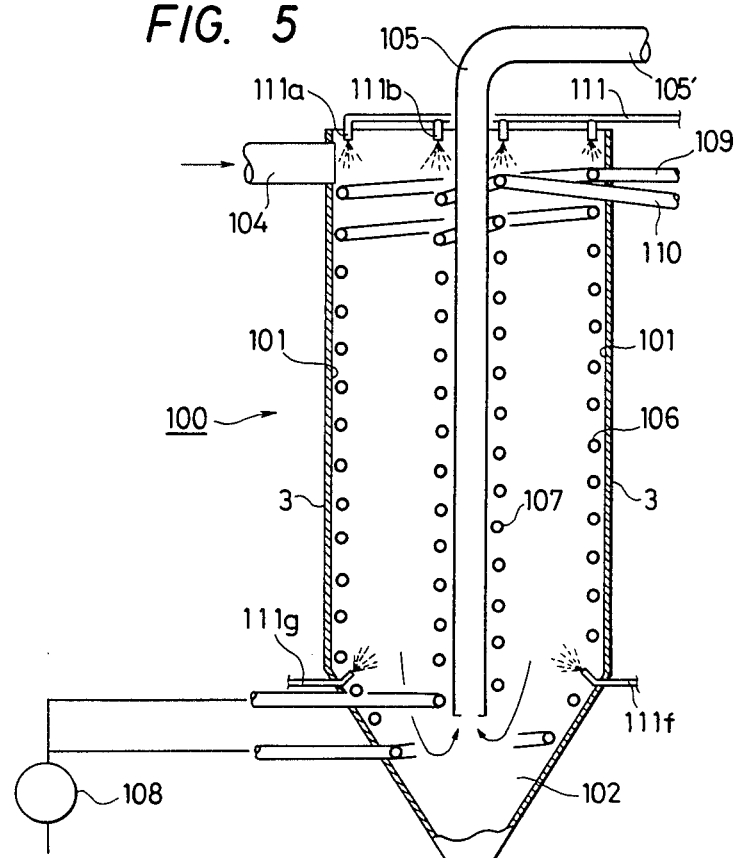
FIG. 5 is an illustration of a heat exchanger which can be provided after the apparatus producing the mist-containing gas.
Figure 6:
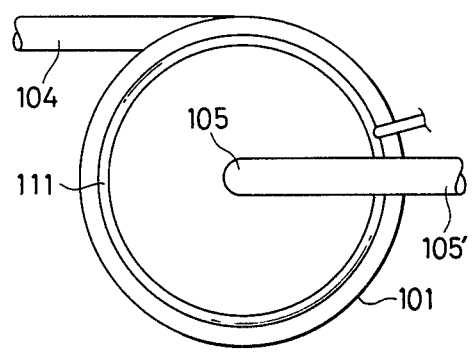
FIG. 6 is a top plan view of the heat exchanger of FIG. 5.

Further, it is possible to raise the air to an optimum temperature as well as make the mist particles smaller to increase its effects, by providing a heat exchanger 100 after the waterdrop-removing cyclone 50, as shown in FIGS. 5 and 6, and passing the mist-containing air through the heat exchanger 100. The heat exchanger 100 will now be described. The center of a barrel 101 is provided with an air discharge pipe 105 which extends vertically. The air discharge pipe 105 communicates with an air duct 105' provided outside the barrel 101. Accordingly, air from an air intake pipe 104 reaches the lower part of the barrel 101 while swirling therein, and rises from the lower part of the air discharge pipe 105 in the direction of the arrows. In addition, the interior of the barrel 101 is provided with an outer pipe 106 and an inner pipe 107. The lower end of each of the pipes 106, 107 communicates with a pump 108 provided outside the barrel 101, in order to pass hot water or cold water therethrough, which is discharged from drain ports 109, 110 provided in the upper part of the barrel 101. A plurality of water injection nozzles 111a, 111b ... formed in a wash water pipe 111 are provided in upper and lower parts of the barrel 101. The nozzles 111a, 111b ... are arranged so as to face the upper and lower sides of the vertical rows of each of the pipes 106 and 107, so that wash water can be jetted out toward the pipes 106, 107 and the inner surfaces of the barrel 101, as well as the outer surfaces of the air discharge pipe 105. A drain pipe 112' is provided in a lower part of the conical portion 102 so that it is possible to drain the wash water, or a drain produced by the cooling of the gas, from the barrel 101. Accordingly, the dust, etc. in the air from the air intake pipe 104 is separated in the barrel 101 by means of a cyclonic effect, and is heated or cooled to an optimum temperature by means of the pipes 106, 107. The air heated or cooled to the optimum temperature is sent out through the air discharge pipe 105. On the other hand, the separated dust and the like can be washed away by supplying water to the wash water pipe 111, and jetting the water out of the nozzles 111a, 111b ...

Since the thus treated air has a large number of mist particles of not more than 0.5 micron suspended therein, any object can be cleaned by treating the object with the air.

The mist particles of not more than 0.5 micron employed in the method of the present invention have an extremely low surface tension and therefore adhere easily to objects or dust suspended in the air. It is presumed that the weight of any dust to which mist particles have adhered will increase, and hence the dust can be removed by means of a blast. In particular, since the method of the invention employs microscopic mist particles, it is possible to remove not only microscopic dust, but also bacteria and viruses, so that an object can be cleaned both physically and biologically. Hitherto, viruses are removed by an air filter or the like. Such viruses are only 0.5 to 0.01μ in size, however, it is impossible to remove them sufficiently by this conventional method. Accordingly, if a room is cleaned by the method of the present invention, the possibility is reduced that people in the room will catch a cold. Thus, the invention is extremely suitable for use in hospitals, pharmacies, laboratories, maternity hospitals, etc.

Moreover, since the method of the present invention makes it possible to avoid the inclusion of various bacteria, this method can be employed for washing the food and apparatuses in food-manufacturing factories. Therefore, the method of the present invention is also extremely suitable for use in food stores, supermarkets and so forth for, for instance, thawing frozen meat and keeping salads, vegetables, fresh fish, and dressed meat. In particular, the method of the present invention makes it possible to manufacture uncooked ham, which conventionally has limitations on the manufacture thereof because of the danger of the inclusion of various bacteria.

I claim:

1. A method of cleaning the inside of a room using a water injection apparatus including a cylindrical enclosure having an interior wall and a water injection pipe supported concentrically by, and extending through, an end wall of the enclosure, the pipe including a plurality of radially directed nozzles disposed along a portion of the pipe located within the enclosure, the method comprising the steps of:

injecting water at a pressure of 0.3 to 5.5 $kg/cm^2$ (gage pressure) from said plurality of nozzles of said injection pipe, each nozzle having an injection opening of a diameter in the range of 0.2 to 8 mm in order to cause the water to strike against said interior wall of the water injection apparatus enclosure, the side wall being 10 to 150 cm away from the nozzles, and thereby form a large number of mist particles;

forming a suspension of mist particles of not less than 2,000,000 particles per cubic foot of air with particle sizes of essentially not more than 0.5 microns by circulating air through said large number of mist particles resulting from said injecting step, while simultaneously separating from said suspension particles of said formed mist of larger size than 0.5 microns by centrifugal effect due to the circulastion of air; and circulating the resulting gas-water suspension created in the water injection apparatus through the room.

2. The method of cleaning the inside of a room according to claim 1, wherein said step of forming a suspension of mist particles comprises creating not less than 5,000,000 particles per cubic foot of air with particle sizes of essentially not more than 0.5 microns.

3. The method of cleaning the inside of a room according to claim 1, wherein said step of forming a suspension of mist particles comprises creating not less than 10,000,000 particles per cubic foot of air with particle sizes of essentially not more than 0.5 microns.

* * * * *